US007698366B2

(12) United States Patent
Schofield et al.

(10) Patent No.: US 7,698,366 B2
(45) Date of Patent: Apr. 13, 2010

(54) METHOD AND APPARATUS FOR FACILITATING THE TRANSPORTATION OF MEDICAL IMAGES ON A COMMUNICATION NETWORK

(75) Inventors: Bruce Schofield, Tyngsboro, MA (US); Franco Travostino, Arlington, MA (US); Indermohan Monga, Acton, MA (US)

(73) Assignee: Avaya, Inc., Basking Ridge, NJ (US)

( * ) Notice: Subject to any disclaimer, the term of this patent is extended or adjusted under 35 U.S.C. 154(b) by 1113 days.

(21) Appl. No.: 10/777,697

(22) Filed: Feb. 12, 2004

(65) Prior Publication Data

US 2005/0182846 A1 Aug. 18, 2005

(51) Int. Cl.
G06F 15/16 (2006.01)
(52) U.S. Cl. ...................................... 709/205
(58) Field of Classification Search .................. 709/205; 370/394.4, 395.42
See application file for complete search history.

(56) References Cited

U.S. PATENT DOCUMENTS

| | | | | |
|---|---|---|---|---|
| 5,920,701 A | * | 7/1999 | Miller et al. ................. | 709/228 |
| 5,991,816 A | * | 11/1999 | Percival et al. ............... | 709/247 |
| 6,041,359 A | * | 3/2000 | Birdwell ..................... | 709/226 |
| 6,671,724 B1 | * | 12/2003 | Pandya et al. ................ | 709/224 |
| 6,975,963 B2 | * | 12/2005 | Hamilton et al. ............. | 702/182 |
| 7,076,540 B2 | * | 7/2006 | Kurose et al. ................ | 709/224 |
| 2002/0006216 A1 | | 1/2002 | Armato, III et al. | |
| 2002/0054568 A1 | * | 5/2002 | Hoogenboom et al. ... | 370/235.1 |
| 2002/0083185 A1 | * | 6/2002 | Ruttenberg et al. ......... | 709/232 |
| 2002/0157092 A1 | * | 10/2002 | Kitsukawa et al. .......... | 709/224 |
| 2003/0083081 A1 | * | 5/2003 | Sanders et al. .............. | 455/466 |
| 2003/0165262 A1 | | 9/2003 | Nishikawa et al. | |
| 2004/0003087 A1 | * | 1/2004 | Chambliss et al. .......... | 709/226 |
| 2004/0073867 A1 | * | 4/2004 | Kausik et al. ............... | 709/219 |
| 2005/0076336 A1 | * | 4/2005 | Cutrell et al. ............... | 718/100 |
| 2006/0056328 A1 | * | 3/2006 | Lehane et al. ............... | 370/315 |

OTHER PUBLICATIONS

R. Hollebeek, *Digital Radiology on NGI WANs, NSCP/NDMA*, University of Pennsylvania, US-UK Workshop on Grid Computing, Aug. 4, 2001 (37 pages).
*Design Considerations for Medical Image Archive System*, (26 pages).

(Continued)

*Primary Examiner*—Larry Donaghue
(74) *Attorney, Agent, or Firm*—Anderson Gorecki & Manaras LLP

(57) ABSTRACT

A method and apparatus for facilitating the transportation of medical images on a communication network includes a medical image transport service (MITS) that may be used to set policy associated with the delivery of medical images on the network. The MITS may be configured to schedule transactions in an equitable manner taking into account the relative priority of the various contending medical image transactions and mediate delivery of images associated with the transactions. The MITS may include a data management service configured to interact with clients to handle transfers on the network, and a network resource manager configured to interface with network devices performing the transport services to enable network resources such as routes, paths, and bandwidth, to be reserved on the network. An administration client enables policy to be set on the MITS to enable operation of the transport service to be controlled.

9 Claims, 4 Drawing Sheets

OTHER PUBLICATIONS

CommsDesign, *FPGA Architecture Ups Intrusion Detection Performance*, Oct. 2003 (10 pages).

Frost & Sullivan, Enabling Picture Archiving Communicaitons System with EMC Automated Networked Storage Solutions, 2003, (7 pages).

Enterasys Networks, *St. John's Hospital Premium Health Care through Enterasys Solutions*, (2 pages).

PC Consultant Group, Inc. PACS&RIS, A practical outline, (4 pages).

White Paper Series, No. 6, version 2, *The DICOM Messaging Implementation of the CMS system*, Feb. 2003 (4 pages).

* cited by examiner

METHOD AND APPARATUS FOR FACILITATING THE TRANSPORTATION OF MEDICAL IMAGES ON A COMMUNICATION NETWORK

CROSS REFERENCE TO RELATED APPLICATIONS

This application is a related to U.S. patent application entitled Method and Apparatus For Monitoring The Transportation of Medical Images on a Communication Network, filed concurrently herewith Ser. No. 10/777,318, the content of which is hereby incorporated herein by reference.

BACKGROUND

1. Field of the Invention

This application relates to communication networks and, more particularly, to a method and apparatus for facilitating the transportation of medical images on a communication network.

2. Description of the Related Art

Radiology has been developed to perform diagnostic imaging in many areas of medicine. For example, diagnostic radiology may be used to visualize organs in the abdomen, such as the digestive system, intestines, kidneys, liver, stomach, and urinary tract, organs in the chest such as the respiratory system and lungs, the central nervous system, the heart and vascular system, soft tissue organs, and the musculoskeletal system such as bones, muscles, joints, back, spine, and neck. Diagnostic radiology may be used to detect numerous types of diseases, such as potential cancer abnormalities, bone densitometry, and many other types of diseases. Additionally, many different types of procedures use radiology to detect the internal structure of the human body. Several examples include arthrography, bone densitometry, magnetic resonance imaging, computed tomography, radiology, intravenous pyelogramy, and other types of non-invasive and invasive imaging.

As technology has advanced, medical imaging has moved from traditional film-based imaging to electronic-based imaging, in which the images produced by the modalities are electronically created and stored. Over time, as the number of modalities has increased and the abilities of the modalities have increased, the amount of data associated with medical images that must be stored and transported over a communication network in the hospital environment has increased dramatically.

A hospital or other medical facility's data communication network may include various computers, servers, nodes, routers, switches, bridges, hubs, proxies, and other network devices coupled together and configured to pass data to one another. These devices will be referred to herein as "network elements." Data is communicated through the data communication network by passing protocol data units, such as data frames, packets, cells, or segments, between the network elements by utilizing one or more communication links. A particular protocol data unit may be handled by multiple network elements and cross multiple communication links as it travels between its source and its destination over the network.

As the amount of medical image traffic on hospital networks has increased, the likelihood that a particular image will experience delay in transmission due to congestion on the network has also increased. One way of avoiding congestion on a network is through the use of reservation protocols. Another way to avoid congestion is to prioritize delivery of protocol data units on the network, such as through the use of Quality of Service (QoS) to differentiate between higher and lower priority protocol data units. Unfortunately, neither of these mechanism allows the network to take into account both the availability of the network resources, and other aspects of the data transfer, such as the type of data, the network participants, who is requesting the data, and numerous other factors that may affect the importance of the data.

SUMMARY OF THE DISCLOSURE

Accordingly, it would be advantageous to provide a method and apparatus for facilitating the transportation of medical images on a communication network. According to an embodiment of the invention, a medical image transport service may be used to schedule the delivery of multiple images and to mediate delivery of those images along with other images in an equitable manner taking into account the relative priority of the various contending medical image transactions attempting to occur simultaneously. The medical image transport service may include a data management service configured to interact with clients to handle transfers on the network and a network resource manager configured to interface with network devices performing the transport services to enable network resources such as routes, paths, and bandwidth, to be reserved on the network. An administration client enables policy to be set on the medical image transport service to enable operation of the transport service to be controlled to thereby affect prioritization of transfers on the network. Numerous other modules may be included and numerous other functions may be performed by the medical image transport service as discussed in greater detail below.

BRIEF DESCRIPTION OF THE DRAWINGS

Aspects of the present invention are pointed out with particularity in the claims. The following drawings disclose one or more embodiments for purposes of illustration only and are not intended to limit the scope of the invention. In the following drawings, like references indicate similar elements. For purposes of clarity, not every element may be labeled in every figure. In the figures:

DETAILED DESCRIPTION

The following detailed description sets forth numerous specific details to provide a thorough understanding of the invention. However, those skilled in the art will appreciate that the invention may be practiced without these specific details. In other instances, well-known methods, procedures, components, protocols, algorithms, and circuits have not been described in detail so as not to obscure the invention.

Figure 1:
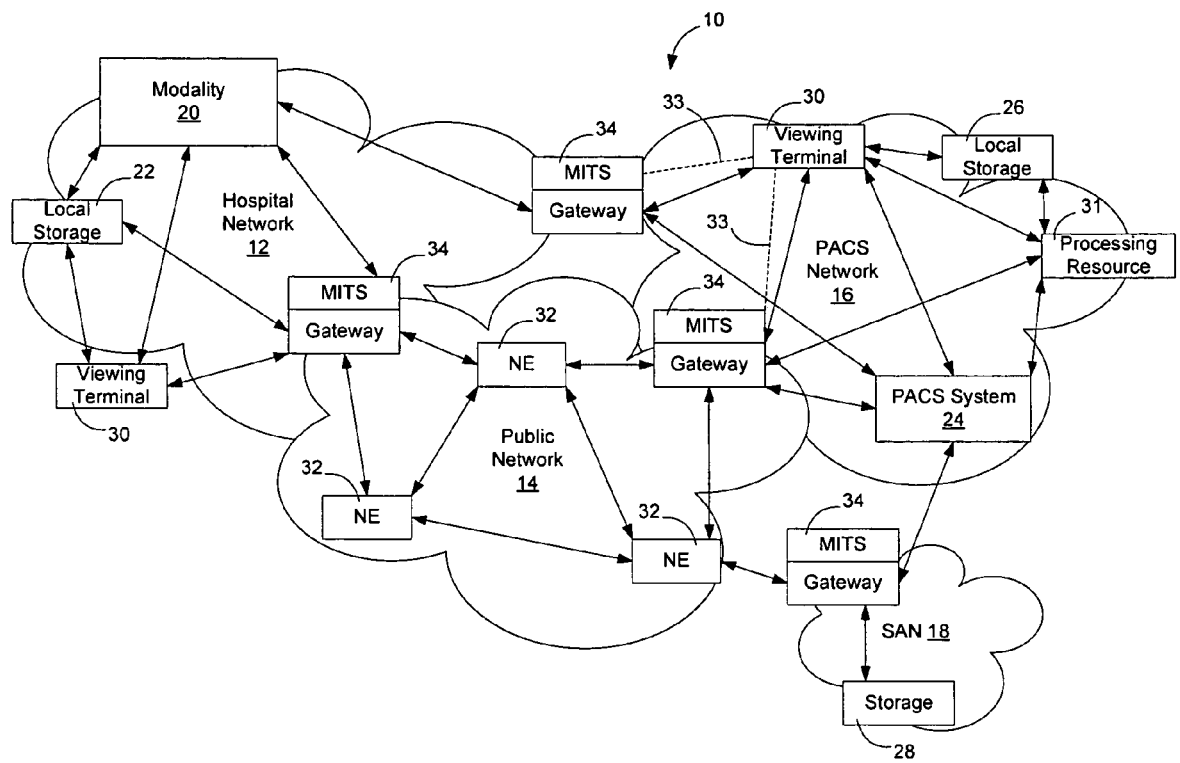
FIG. 1 is a functional block diagram of an example of a medical communication network including a medical image transport service according to an embodiment of the invention.

FIG. 1 illustrates an example of a medical communication network including a medical image transport service according to an embodiment of the invention. In this example, the medical image transport service is configured to facilitate transfers of data between a data source such as a modality and a data target, such as a Picture Archiving and Communication System (PACS) system or a storage system. A PACS system is a conventional system on many medical networks that is specifically designed to store medical images and to serve the medical images on the communication network when required. As discussed in greater detail below, a medical image transport service, according to an embodiment of the invention, enables the transportation of medical images on the network to be controlled, scheduled, prioritized, and monitored to thereby enhance performance of the medical network in connection with transportation of medical images.

As shown in FIG. 1, a network 10 configured to transport medical images may include one or more domains such as a hospital network domain 12, a public network domain 14, a PACS network domain 16, and a storage area network (SAN) domain 18. Other domains may be included as well, and the invention is not limited to a network including all or only these several illustrated domains. When medical images are to be transported across the network 10, enforcement of policy on the several domains and coordination between the domains for transmission of the medical images from a data source to a data target may present significant challenges. One simple way to transmit medical images in a network such as the network illustrated in FIG. 1 is to use Internet Protocol or another routing protocol to find an available path through the network. Transmission of images in this manner relies on the end devices to set the proper quality of service level for the transmissions, and does not provide for coordinated control over the transmission of medical images between the various network elements.

According to an embodiment of the invention, a medical image transport service is deployed on the network to coordinate transportation of medical images on the communication network, such as by scheduling transmissions, obtaining network resources to accommodate the scheduled transportations, and monitoring the transmission and network participants, to coordinate delivery of the medical images. Additionally, when necessary, the medical image transport service may take corrective action on the network to transport the requested image on a different route through the network or to secure the requested image from another data source. The medical image transport service may also perform other functions on the network, as discussed in greater detail below.

In the network illustrated in FIG. 1, one or more modalities 20 are configured to generate images for transportation on the network. Examples of several common modalities include x-ray machines, CAT scan machines, ultrasounds, and numerous other types of modalities as discussed in greater detail above.

Images generated by the modalities may be stored in a number of places on the network. For example, the images may be stored in a local storage 22 associated with the modality or configured on the hospital network to which the modalities are connected. Alternatively, the medical images may be transported across the network to a PACS network and stored in a PACS system 24 or local storage on the PACS network 26. Similarly, the medical images may be transported across the network to the storage area network 18 and stored in storage 28 on the storage area network. Other storage solutions may be provided as well and the invention is not limited to a network including all or only these several identified storage possibilities.

Images generated by the modalities may also be transported directly to one or more viewing terminals 30 to be reviewed by medical personnel. For example, a medical image generated by an x-ray modality may be transmitted to a surgeon preparing for surgery in another room so that the surgeon is able to understand the nature of the trauma to the patient and properly prepare for the surgery. Similarly, medical images stored on one or more of the storage solutions may need to be retrieved at a later time and displayed for review at a viewing terminal. Other types of transactions may be commonly performed as well, such as retrieval of prior images, clinician retrieval of images or image enhancements, transfers between medical personnel to obtain second opinions on images, and numerous other transactions. The invention is not limited to a particular transaction type or to the particular transactions mentioned herein.

Images generated by the modalities may be processed prior to being stored or prior to being viewed by medical personnel. For example, it may be desirable to perform edge resolution, contrast enhancement, or other operations on a medical image. Similarly, it may be desirable to combine multiple images into one file to enable greater three dimensional imaging to be provided from the several images. Optionally, these processes may be performed by a network resource deployed on the network, such as processing resource 31. Inclusion of a processing resource enables the medical image transport service to mediate advanced transactions involving image manipulation without further burdening the PACs server or other deployed equipment. The processing resource may be associated with a network element such as a router or switch, or may be a self contained network resource.

In all of these situations and numerous others, the medical images are required to be transported from one place on the network to another place on the network 10. As used herein, the term "data source" will be used to describe the place where the data originated and the term "data target" will be used to describe the intended destination of the data. For example, where a modality is generating an image that is to be transferred to storage, the modality would be the data source and the local storage 22, the PACS system 24, the PACS local storage 26 or the SAN storage 28 would be the data target. Similarly, where a medical image is to be displayed, one of the storage devices or the modality may be considered the data source, and the viewing terminal may be considered the data target. Where a more complex transaction is to take place, such as the delivery of data from a modality 20 to the processing resource 31, and then from the processing resource to the PACS server 24, each portion of the transaction may be considered to have a data source and a data target.

As shown in FIG. 1, the various elements of the network 10 are interconnected by one or more network elements 32 configured to transport data on the network. The network elements may be gateways interfacing between two or more network domains or may be network elements configured to operate wholly within one domain. The invention is not limited by the number or configuration of the network elements.

According to one embodiment of the invention, a medical image transport service 34 is deployed on the network and configured to interface with the network elements to enable the transportation of medical images on the network to be facilitated. As described in greater detail below, facilitating the transportation of medical images may encompass many different aspects associated with transporting the images, including scheduling transmission of the images, obtaining bandwidth for their transmission, monitoring the transmission, notifying and taking corrective action when transmission is interrupted, and performing many more functions associated with transporting images on the network. These and other aspects of the medical image transport service will be described in greater detail below in connection with FIGS. 2-6.

The medical image transport service may be deployed on a gateway network element between two or more of the network domains, may be deployed as an independent service on the network and connected to the network, or may be deployed on one or more network elements within one or more of the domains. The medical image transport service may also be associated with the viewing terminal, PACS system, modality, storage resource, or other participant on the network. The invention is not limited to where on the network the medical image transport service is deployed. According to one embodiment of the invention, the medical image transport service may be implemented as a blade server, associated with a content switch on the network. The invention is not limited in this manner, however, as described in greater detail below.

Figure 2:
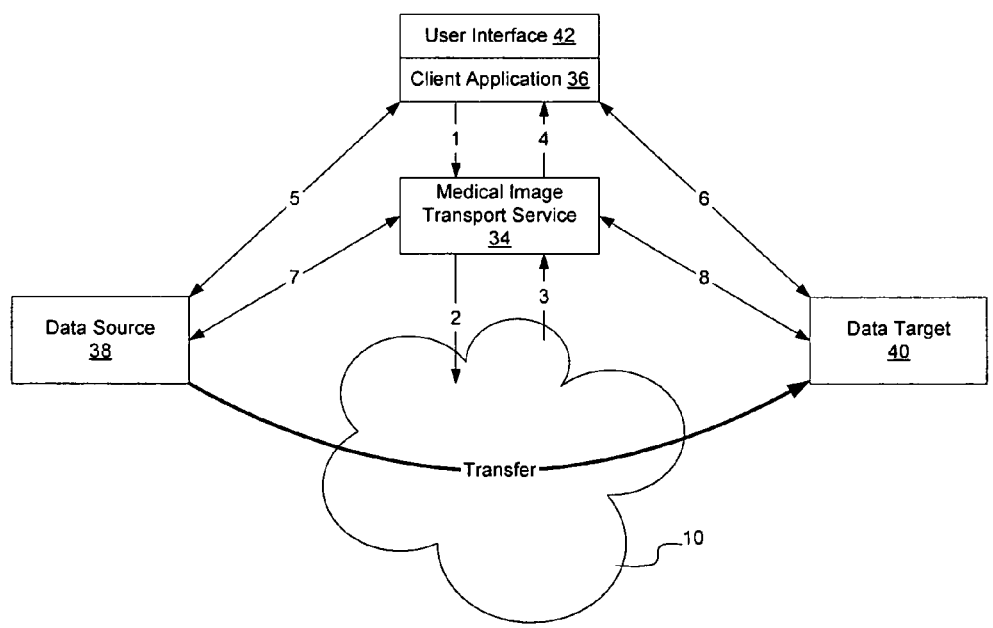
FIG. 2 is a functional block diagram of a network architecture including a medical image transport service according to an embodiment of the invention.

FIG. 2 illustrates a functional block diagram of a network architecture including a medical image transport service 34 according to an embodiment of the invention. As shown in FIG. 2, the medical image transport service is configured to interface with a client application 36 to enable the client application to facilitate the transmission of medical images from one or more data sources 38 to one or more data targets 40. Although an implementation of the invention will be described in part herein in connection with facilitating a single transmission on the network from a data source to a data target, the medical image transport service may be configured to perform other transactions as well. For example, the medical image transport service may be configured to coordinate multiple transfers between different sources and targets to achieve more complicated transactions. One example of a more complicated transaction may be, for example, to obtain medical images, pass the medical images to network attached computational resources, retrieve the results of the computation, and return the results to storage and/or to a viewing terminal. Thus, the invention is not limited to performing one dimensional transactions from a data source to a data target, but may be used to facilitate multi-dimensional transactions involving pluralities of transfers from data sources to data targets. As indicated above, the data sources may be modalities, storage resources, or processing resources, and the data targets may similarly be storage resources, processing resources, and viewing terminals. Thus, complex transactions may be accommodated and managed in the network through the medical image transport service. To facilitate an understanding of how the invention may be used in a particular context, a transaction involving the transmission of a medical image from a data source to a data target will first be described, and then larger transactions will be described in subsequent embodiments.

As shown in FIG. 2, when a transaction is to occur on the network to transport a medical file from a data source to a data target, the client application responsible for the transaction will access the medical image transport service (arrow 1). Optionally, the client application may also access the data source 38 and/or data target 40 although, depending on the implementation, the medical image transport service may be configured to interface with and coordinate the transfer between these elements as well.

The client application 36 may be associated with an user interface 42 to enable users to access the client application to affect transactions on the network. Additionally, or alternatively, the client application may interface with or be associated with other programs running on the network to enable those programs to affect transfers on the network. The client application may be associated with a modality, with a viewing terminal, with one or more storage elements, or with another program running on the network. For example, a radiologist at a viewing terminal may be provided with an user interface to enable the radiologist to control the client application to cause medical images to be downloaded to a viewing terminal in his vicinity. Alternatively, the radiologist may control the client application to cause medical images to be moved from an archive storage to a local storage to make the images more accessible, e.g. during an operation. Thus, the client application may be associated with one of the users or network elements on the network, or may simply be associated with a management terminal and used to move data through the network for the use by other processing devices or access devices. Optionally, the medical image transfer service may be associated with the PACS server, although the invention is not limited to this embodiment.

The client may not know where the data source actually resides on the network, or there may be replicas of the data that reside in a number of places on the network. For example, the requesting client may not know how the data is stored on the network, but know the name of the dataset or the content of the dataset that it would like to request. In this instance, the medical image transport service may interact with a replica location service (not shown) to find the location(s) on the network of the actual files that make up the named data set. Then, the medical image transport service may choose a convenient source location based on a number of factors, such as the physical proximity of the data source to the data target, the availability of the data source to fulfill the request, the cost associated with obtaining the data from the data source, the availability of the network resources to transport the requested data from the selected data source to the intended data target, and many other factors. Optionally, after the data set has been moved, the replica location service may be notified that another copy of the data exists, and its location. One replica location service is currently being developed in connection with the GRID initiative (discussed below), although other replica location services may be used as well.

The medical images may be formatted using a conventional medical format such as DICOM as described in greater detail above. The invention is not limited to medical images in the DICOM format, however, as other formats may be used as well.

The data source and data target may be associated with ftp server daemons or other conventional data transfer engines configured to send and receive data on demand. The transfers may take place using an underlying file transfer mechanism over the reserved and allocated network resources. Several available transfer mechanisms include:

DICOM
File Transfer Protocol (FTP);
GRIDftp;
Fast Active Queue Management Scaleable TCP (FAST);
TSUNAMI (a protocol that uses TCP for transferring control information and UDP for data transfer);
Simple Available Bandwidth Utilization Library (SABUL)—a UDP-based data transfer protocol;
Blast UDP;
Striped SABUL (P-SABUL); and
Psockets.

Other transfer mechanisms may be used as well and the invention is not limited to an implementation that uses one of these several identified protocols. For example, in one embodiment of the invention, bandwidth and other resources on the network may be obtained by using one or more of these protocols to perform rate limiting, set appropriate quality of service values end-to-end, and perform translation from domain to domain across the network (both layer 1 and layer 2) to obtain sufficient resources to accommodate the transmission. Additionally, in an optical network such as a SONET network, a protocol such as the Resilient Packet Ring protocol (IEEE 802.17) may be used alone, or in combination with Multi-Protocol Label Switching (MPLS), to obtain network resources for the transmissions. The invention is not limited to this particular example, however, as other protocols and other mechanisms may be used to interface with the network resources.

Once the client application has passed the requested transaction to the medical image transport service, the medical image transport service will contact the network resources (arrow 2) to determine the availability of the network and to reserve bandwidth and other resources for the requested transaction (arrow 3). Once the necessary resources have been reserved, the medical image transport service may report back to the client application (arrow 4) and allow the client application to coordinate delivery of the medical image between the data source and the data target (arrows 5 and 6). Alternatively, the medical image transport service may coordinate with the data source and data target (arrows 7 and 8) to effect transfer of the medical image. Optionally, advanced scheduling may occur to allow transactions to occur on demand, in the future, or in an unconstrained nature. The medical image transport service may coordinate with the network resources, data source, and data target in any desired order and the invention is not limited to interfacing with these components in any particular order.

According to one embodiment of the invention, the medical image transport service may be configured to understand the work flow associated with the transmission of medical images to automatically adjust network parameters such as bandwidth and quality of service to meet the requirements of the applications. By understanding the work flow on the network, the network can understand not only what is happening, but what is going to happen next, so that even "on-demand" image transport may be "scheduled," by anticipating the on-demand event or the likelihood of the on-demand event, and obtaining bandwidth and other network resources to accommodate it.

The medical image transport service may be configured to receive requests for data transfers with requested scheduling constraints and policy tags, prioritize transfers between competing requests, and fulfill requests by scheduling and allocating resources on the network. The policy tags may be used to differentiate between transfers, as discussed in greater detail below, to enable the transfers to be differentiated and prioritized on the network. The medical image transport service may also monitor the data transfer and optionally manage the data transfer.

According to one embodiment of the invention, the medical image transport service may allow data transfers to occur:
on demand (right now);
rigidly in the future (e.g., "tomorrow precisely at 3:30 am");
loosely in the future (e.g., "Tuesday, after 4 pm but before 6 pm"); and
constrained by events (e.g., "after event A starts or event B terminates");

although many other types of reservations may be made as well, and the invention is not limited to a system that is able to implement these or only these particular types of network resource reservations. A reservation request that is not rigidly fixed with precise required parameters will be referred to herein as under-constrained. In this context, an under-constrained resource reservation request enables the request to be fulfilled in two or more ways rather than only in one precise manner. An example of an under-constrained request may be to transfer all medical images for a particular patient to a particular terminal in an operating theatre by a scheduled time.

The medical image transport service also includes hardware and software configured to enable it to query the network for its topology and characteristics. It includes one or more routing modules to plan available and appropriate paths between requested endpoints in (or near) requested time windows; and the ability to allocate specific segment-by-segment paths between endpoints, and to relinquish them when the data transfer is done or when the user decides to cancel a reservation or request.

The medical image transport service can be instantiated in many forms on the network, such as a stand-alone Web Service, or as a Web Service configured to interact with other Web Services. For example, the medical image transport service may interact with other Web Services, such as those which manage disk storage and those which manage computational resource availability, in order to coordinate all of these disparate resources to fulfill a submitted request. In one embodiment, the medical image transport service is instantiated using the Globus Toolkit, such that components are configured with Open Grid Services Interface (OGSI) compliant application interfaces within the Open Grid Services Architecture (OGSA). The invention is not limited to a GRID embodiment, however, as other embodiments may be utilized as well. For example, the medical image transport service may be instantiated as a web service configured to interact with network resources and data resources on the network without being configured to implement GRID functionality.

Figure 3:
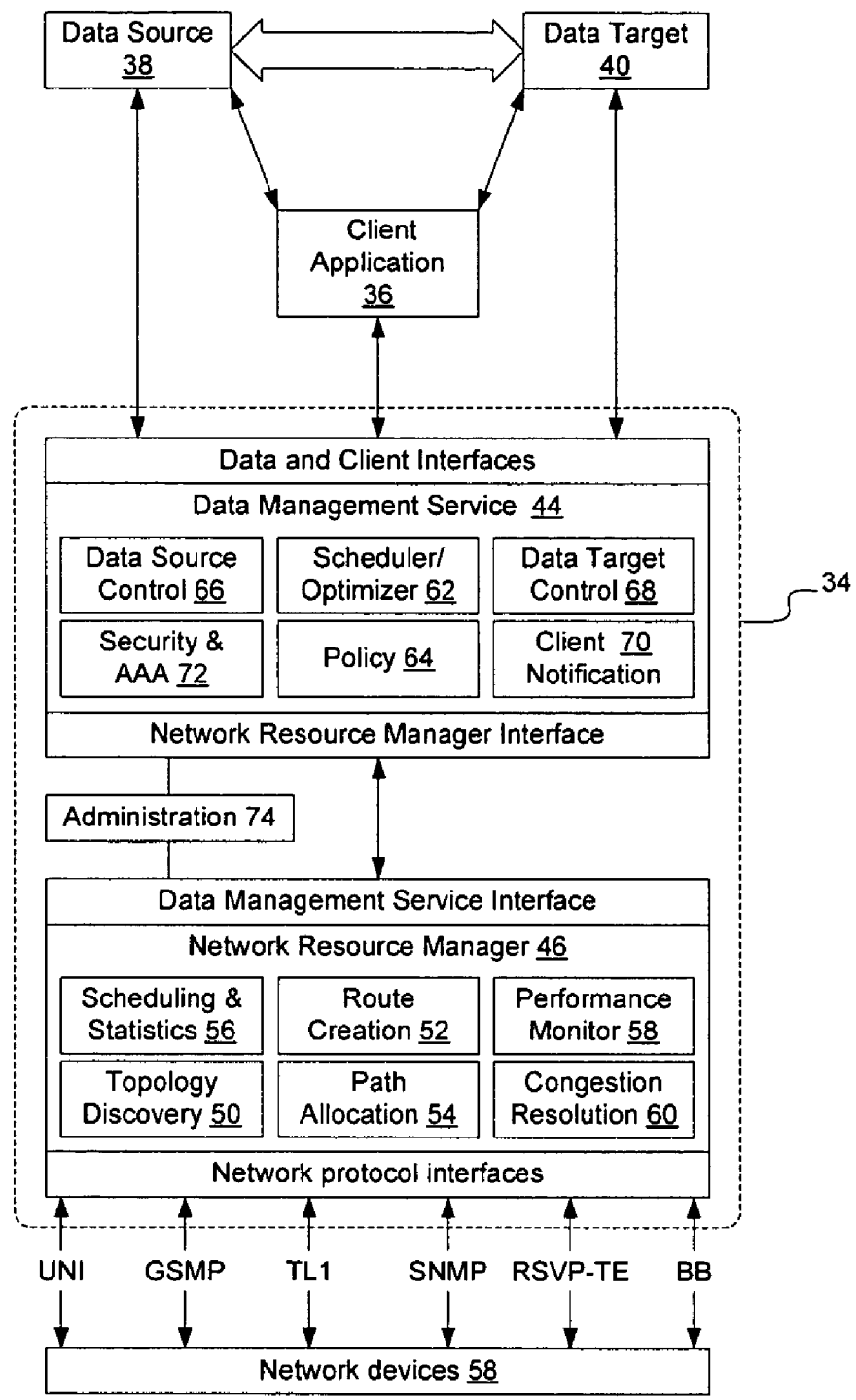
FIG. 3 is a functional block diagram of the network architecture of FIG. 2 showing the medical image transport service in greater detail according to an embodiment of the invention.

FIG. 3 illustrates an architecture that may be used to implement an embodiment of the invention. As shown in FIG. 3, in this embodiment, a client application 36 interacts with a medical image transport service 34 to effect a data transfer between a data source 38 and a data target 40 over a network. Interactions between the client 36 and the medical image transport service 34 may take place using a communication protocol such as Simple Object Access Protocol (SOAP), Extensible Markup Language (XML) messaging, Hyper Text Transfer Protocol (HTTP), Data Web Transfer Protocol (DWTP) or another conventional protocol. The invention is not limited to the particular protocol used to communicate between the client application 36 and the medical image transport service 34.

In the architecture of FIG. 3, the medical image transport service 34 includes two major portions: a data management service 44 and a network resource manager 46. The data management service 44 is generally responsible for interfacing the client 36, data source 38, data target 40, and other application level and resource level network constructs. The network resource manager 46 is generally responsible for interfacing the network resources 48 forming the network 10, such as routers, switches, bridges, hubs, management stations, etc. that are used to transport and manage the transportation of data on the network 10. The data management service 44 and the network resource manager 46 may be implemented on a particular network element on the network or may be implemented on different network elements on the network 10.

The network resource manager may be required to interface with many different types of network resources and may need to communicate with the networks and network devices using a number of different interface and management protocols. In FIG. 3, the network resource manager is illustrated as being configured to communicate with network devices using the following protocols:

User to Network Interface (UNI), a protocol developed to interface Customer Premises Equipment (CPE) such as ATM switches and optical cross connects with public network equipment;

General Switch Management Protocol (GSMP), a general Internet Engineering Task Force (IETF) protocol configured to control network switches;

Transaction Language 1 (TL1), a telecommunications management protocol used extensively to manage SONET and optical network devices;

Simple Network Management Protocol (SNMP), an IETF network monitoring and control protocol used extensively to monitor and adjust Management Information Base (MIB) values on network devices such as routers and switches;

Resource Reservation Protocol (RSVP) or RSVP-Traffic Engineering (RSVP-TE), a signaling protocol used in Multi-Protocol Label Switching (MPLS) networks, that allows routers on the MPLS network to request specific quality of service from the network for particular flows, as provisioned by a network operator; and Bandwidth Broker, an Internet2 bandwidth signaling protocol.

Other conventional or proprietary protocols may be used as well, and the invention is not limited to these particular identified protocols.

The network resource manager 46 includes a topology discovery module 50 configured to perform topology discovery on the network to discover how the underlay network elements are configured and what resources are deployed throughout the network. The topology discovery module may also discover available bandwidths on the network and detect areas of congestion on the network.

The network resource manager 46 also includes a route creation module 52 configured to create routes through the underlay network, and a path allocation module 54 to enable the routes to be populated with paths for particular data transfers on the network. These modules coordinate with the topology discovery module 50 to avoid areas of congestion on the network and a scheduling module 56 to enable the creation of routes and paths to be performed in connection with the required schedule maintained by the scheduling module, as directed by the data management service. The path allocation module 54, in addition to allocating paths, also effects reservations on the allocated paths so that the paths can be used to effect the transfer of medical images between the data source and data target.

The network resource manager 46 may also include additional modules such as a performance monitor 58 and a congestion resolution module 60. The performance monitor may be provided to monitor data transfers on the network to determine if one or more of the data transfers was unable to be completed for a particular reason such as a network failure or congestion. Additionally, the performance monitor may be used to collect statistics on the network relating to traffic patters. The statistics may be collected based on the time of day, day of the week, seasonal variations, the lunar calendar, or any number of other bases. The statistics collected by the performance monitor may be used to build histograms on a daily, weekly, monthly, or other time scale, which may be passed to the data management service for use in connection with setting policy on the network to enable the policy to take into account expected traffic patterns on the network.

The congestion resolution module 60 coordinates with the topology discovery module 50 and performance monitor 58 to respond to indications of congestion on the network, and coordinates with the route creation and path allocation modules 52, 54 to obtain new resources for the transmission of medical images around areas of congestion on the network. The congestion resolution module, in coordination with the other modules of the network resource manager 46, thus is able to diagnose problems on the network, determine which flows are affected by the network problems, obtain new resources for those flows, and cause the flows to use the new resources.

The data management service 44 interfaces with the client application 36 to receive requests and optionally coordinates with the data source 38 and data target 40 to affect the transfer of the requested medical image(s) over resource provided by the network resource manager 46. The data management services includes a scheduler/optimizer 62 configured to schedule the transmission of medical images between the data source and data target and maintain work-flow information associated with medical image transactions on the network. Statistics may be used, in this context, to anticipate the likelihood of particular types of transactions and pre-allocate or pre-schedule resources for anticipated transactions. Additionally, transaction patterns (i.e. sequences of particular transactions that occur frequently) may be stored and used to anticipate upcoming transactions which may be scheduled or otherwise anticipated on the network. When the medical images are to be delivered in real time, scheduling the transmission of medical images may cause the medical images to be delivered as soon as possible. Where a portion of the medical images to be delivered in real time have a high priority, and others are to be delivered in real time with relative lower priority, the scheduler may organize transmissions to take into account the relative priority of the requests. Additionally, where the medical image transport service is configured to schedule under-constrained requests that may occur at a future point in time, the scheduler/optimizer module 62 may be configured to optimize scheduling of the several requests to accommodate the requests in according to the specified constraints.

The data management service 44 may also include a policy module 64 that enables the data management service to discern higher priority requests from lower priority requests, and to cause higher priority requests to be provided a higher quality of service and enhanced status in the scheduler/optimizer module. Specifically, the policy module 64 may enable the data management service to look at the request to determine what application generated the request, who is running the application, where the application is being run, why the application is being run or why the image is being requested, the time of day, and other priority indications associated with the request. For example, the data management service may be configured to differentiate between requests generated by a terminal in an operating room and an identical terminal in a radiologist's office. Likewise, the data management service may be configured to differentiate between requests generated by a surgeon and a radiologist, if the two medical personnel were to log into the same terminal at different times. Numerous other prioritization factors may be implemented in the policy module as well and the invention is not limited to these several described factors. Policy values may be set in the policy module for example by the network administrator, to enable the data management service to prioritize or otherwise give preferential treatment to requests on the network.

The data management service may include a data source control module 66 and a data target control module 68 to enable the data management service to coordinate transfer between the data source and data target. For relatively simple transactions, the data source control module may simply instruct the data source to transfer the data over a particular path using particular parameters, to a particular destination. In more complicated transactions, more extensive control may be warranted such as by instructing the data source to prefetch the data to keep it in a local cache or to otherwise make the data ready for transfer over the network. Where the transaction is a multipart transaction, for example where data is to be transferred to an intermediate resource for manipulation or computation prior to being transferred to the ultimate target, the data source and data target control modules, in connection with the scheduler module, allow the data management service to maintain information about the transaction to ensure the transaction is able to be accomplished on the network. Optionally, the scheduler/optimizer 62 may be used to coordinate more complicated transactions on the network, for example by maintaining a record of the transaction and associated work-flow on the network.

Optionally, the data source control module 66 and the data target control module 68 may be configured to implement rate limiting to cause the data source and/or data target to stop sending or stop requesting data where the network or a particular part of the network is experiencing congestion and the data source and/or data target are participating in the transmission of relatively lower priority medical images. The invention is not limited in this manner, however.

The data management service may also include a client notification module 70 to enable the client to be notified of the status of the request. Radiologists and other medical personnel may prefer to work in an efficient manner to enable them to review a particular number of images in a given period of time. Occasionally, network problems or problems with the data source or data target may cause a transaction to be delayed. By providing a performance monitor 58 on the network resource manager 46 and a client notification module 70 on the data management service 44, the medical image transport service 34 is able to identify the source of the problem and notify the client application of the problem. Optionally, where the problem is isolated on the network, the congestion resolution module 60 may be able to find a new route around the problem on the network. Alternatively, where the problem is isolated on the data source, the data source control module 66 may be able to find an alternative source for the data and obtain the data from the new source. In either event, the client notification module may enable the client to be informed of the nature of the problem, the steps the medical image transport service is taking to correct the problem, and optionally an estimate of when the problem is likely to be resolved. Where the problem exists on the sole source of the data, the data target, or the client, the client may be notified of that as well.

There may be instances where the network that will carry the medical image is also the network that will carry the notification to the client that the network is experiencing problems. According to an embodiment of the invention, the client notification module may be connected to an external communication network, such as a telephone network, an e-mail network, or other electronic messaging network, to enable the notification to occur outside of the network experiencing failure. Optionally, both types of notification may be available to the medical image transport service to enable notification to occur preferentially through the network 10, and alternatively through other available communication channels. This redundant network is illustrated in FIG. 1 by the dashed lines 33 interconnecting several of the medical image transport service 34 and the viewing terminal 30.

Medical images are generally required to be transmitted in a secure manner and delivered only to authenticated and authorized individuals or machines. To accommodate these requirements, according to an embodiment of the invention, the medical image transport service may include a security/AAA module 72 to enable the medical image transport service to participate in secure transactions on the network. This module may be located in the data management services portion of the medical image transport service as illustrated, may be located in the network resource manager portion, or may be available to both portions. The invention is not limited to where, logically, the security/AAA module is included in the medical image transport service.

The AAA service module 72 may be provided to enable the client applications to be authenticated on the network, enable the user of the client application to be authenticated on the network, enable the network components such as the data management service and the network resource manager to ascertain whether the user of the application is authorized to perform transactions on the network, and to allow accounting entries to be established and associated with the proposed transaction. Accounting entries may enable particular data transfers to be associated with particular users and with particular access terminals to enable transactions to be reconstructed at a later time if required. Additionally, a security service may be provide to enable encryption and other security services to be provided in connection with the request or data transfer to enable the transaction to occur in a secure fashion and to enable the data to be protected during the transfer. For example, the security module may support the creation of Virtual Private Network (VPN) tunnels between the various components involved in securing the transfer of data across the network. Numerous other security services may be performed as well and the invention is not limited to an architecture having only these several discussed security services.

Once a transfer has been scheduled and the bandwidth reserved on the network, the data occurs, assisted if necessary by the medical image transport service. For example, the medical image transport service may assist in the transfer of the data by checking to see if the source file exists, reporting on parameters associated with the source file such as its size and permissions, optionally checking with the data target to see if there is enough disk space to hold the transfer, causing the transfer to happen, reporting back on the status of the transfer when queried or at predetermined intervals, and informing the client that a transfer has been completed or if there is a problem with the transfer. Other functions may be performed as well and this list of functions is intended merely as an example of some of the functions that may be performed by the medical image transport service. According to one embodiment of the invention, to make the components compatible with GRID computing technology, all application layer interfaces are configured to be OGSI compatible. This enables the network resource manager and data management service to be treated as resources in a GRID computing environment, so that they may be accessed by the applications either through GRID resource manager or directly in much the same way as an application would access other GRID resources. The invention is not limited to an embodiment that is GRID compatible, however.

An administrative client 74 may be provided to enable an administrative interface to the medical image transport service to be used to set values, issue commands, control, and query the underlying services. The administrative client 74 may be used to perform various services on the medical image transport service, such as to query the medical image transport service, debug problems, set policy values in the policy module 64 and elsewhere in the medical image transport service, adjust the configuration of the medical image transport service, and perform other management operations while the medical image transport service is running. For example, the administrative client may be able to obtain information from the medical image transport service such as the jobs/routes scheduled for a particular client, jobs currently running, current topology model, current parameter list, and many other types of information. The invention is not limited to a particular implementation of the administration client 74.

Figure 4:
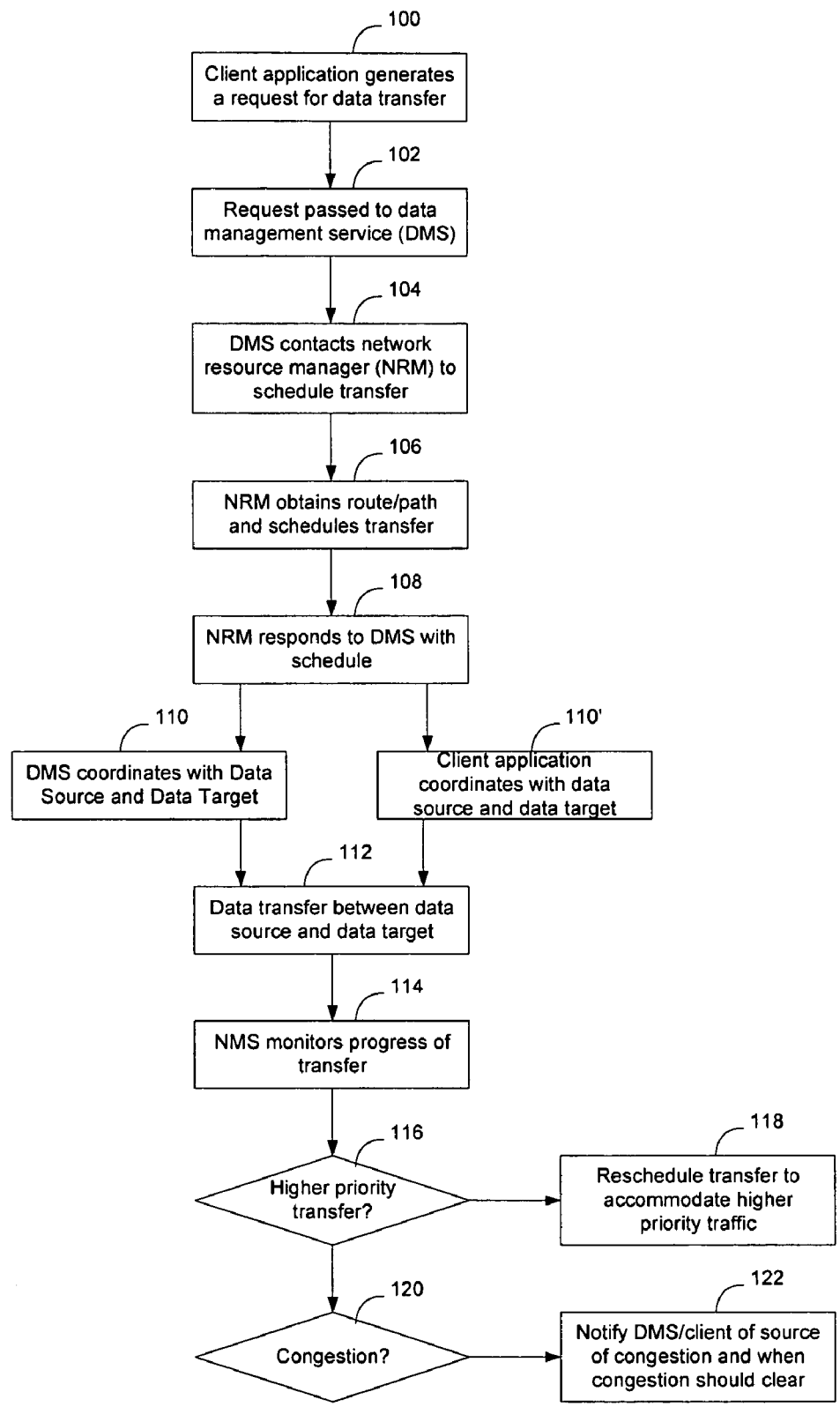
FIG. 4 is a flow diagram illustrating a process of scheduling resources to accommodate medical image transport on the network architecture of FIGS. 2 and 3 according to an embodiment of the invention.

FIG. 4 illustrates a flow chart of an example of a how requests may be processed by the medical image transport service of FIGS. 1-3. As shown in FIG. 4, a client application generates a request for a medical image data transfer (100). This request may specify various parameters as discussed above, such as the time for delivery, where the data should be delivered, the specific medical image, the set of medical images or group of medical images, policy tags such as the perceived relative importance, credentials associated with the person making the request and the destination of the transfer, and numerous other parameters. The request is passed from the client application to the data management service (102) where authentication, authorization, accounting, and other preliminary functions are performed. The request is then passed to the network resource manager (104) to cause the network resource manager to schedule the transfer. The network resource manager obtains a route/path through the network for the transfer, based on the current network conditions, historical network conditions, and estimated future network conditions, and allocates the route/path to the data transfer. The network resource manager also secures the resources on the network by interacting with the network elements to reserve bandwidth for the transfer (106).

Once bandwidth has been reserved, the NRM responds to the DMS with an indication that resources have been obtained and provides particular information associated with the reservation (108). For example, where the reservation has been made on a particular path through the network, the data source will need to be provided with information to enable it to use that path. Standard routing information may be provided in connection with this process.

Where the medical image transport service is to handle the transfer on behalf of the client application, the DMS will coordinate with the data source and data target to facilitate the transfer (110). Alternatively, the client application may perform this process (110'). At the schedule time, the transfer commences (112). Optionally, according to one embodiment of the invention, the medical image transport service may monitor the progress of the transfer (114). In the event of a higher priority transfer (116), the medical image transport service will reschedule the transfer to accommodate the higher priority traffic (118). In the event of congestion or a network failure (120), the medical image transport service will attempt to route around the congestion, obtain the data from another source, or take other corrective action to enable the medical images to be supplied to the client application (122). The client application may be informed of the progress at various stages throughout the process or only when there is a problem or failure on the network that affects the medical image transfer.

As discussed briefly above, transactions to be handled by the medical image transport service may be relatively small, such as the transfer of a single medical image from a PACS server to a viewing terminal. However, the medical image transport service is not limited to performing single image transfers. Rather, according to an embodiment of the invention, the medical image transport service may be used to schedule the delivery of multiple images and to mediate delivery of those images along with other images in an equitable manner taking into account the relative priority of the various contending medical image transactions attempting to occur simultaneously. For example, the medical image transport service may deliver images from a PACS server to a viewing terminal serially to be viewed by a technician at the viewing terminal. The images to be delivered may be selected by the technician in groups, by patient, or in any other manner. Alteration of the relative priority of the images may be set through the use of priority tags associated with the requests and through adjusting policy parameters in the policy module 64 through the administrative client 74.

Additionally, as modalities have increased in complexity and their abilities have increased, it has become possible to perform various types of signal processing on the medical images. One emerging type of signal processing is an attempt to combine images from multiple different modalities to enable more detailed viewing of three dimensional structures in the body to be visualized. This processing may take a considerable amount of time. By enabling the transaction to specify the particular type of processing, the medical image transport service may coordinate delivery of the medical image files to a processing resource on the network, delivery of appropriate code to the processing resource (where applicable) and delivery of the processed image from the processing resource to the data target. Accordingly, providing advanced scheduling of the medical image transport service on a medical network enables advanced transactions to be performed in connection with medical images without extensively modifying the modalities or PACS systems. Additionally, enabling these functions to be performed by a network service makes the functions available for all modalities on the network without requiring the modalities to be upgraded to perform the new processing functions.

Figure 5:
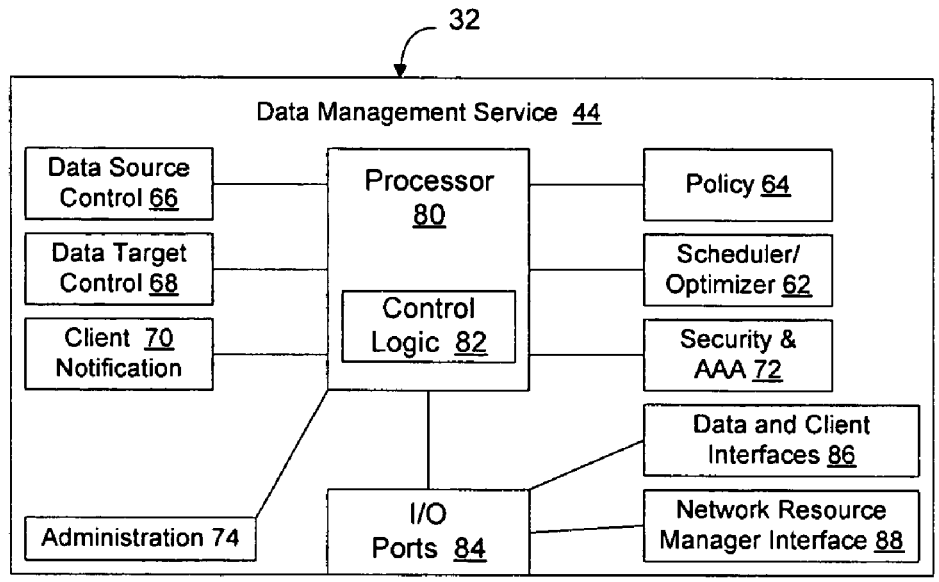
FIG. 5 is a functional block diagram of a network device implementing a data management service portion of the medical image transport service of FIG. 3 according to an embodiment of the invention.
Figure 6:
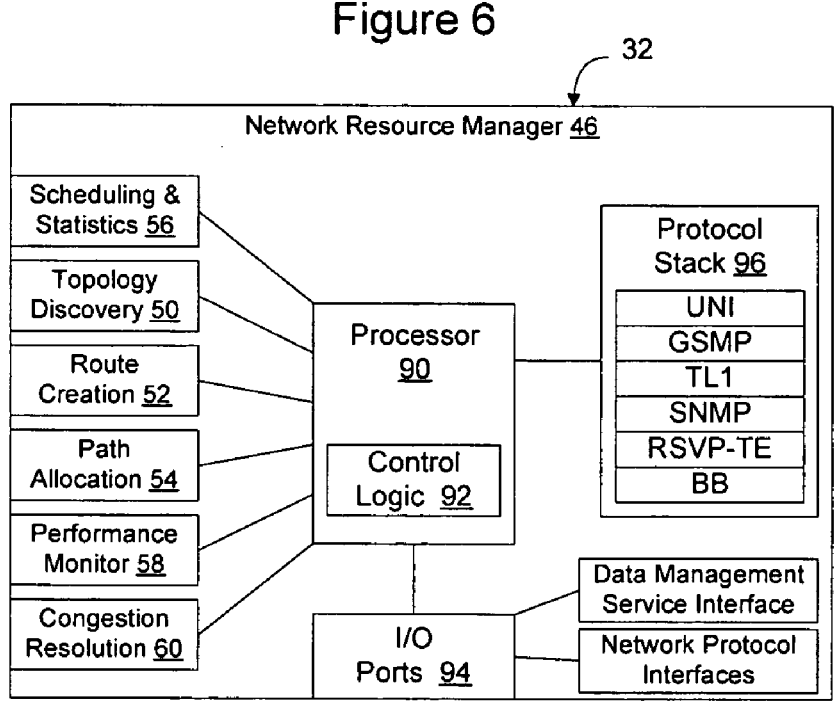
FIG. 6 is a functional block diagram of a network device implementing a network resources manager portion of the medical image transport service of FIG. 3 according to an embodiment of the invention.

FIGS. 5 and 6 illustrate embodiments of network elements configured to implement the data management service and the network resources manager according to an embodiment of the invention. These network services may be embodied in separate network elements, as illustrated, or may be housed in the same network element and share resources such as processor, memory, and other computing resources.

In the embodiment illustrated in FIG. 5, the data management service 44 is configured to be implemented on a network element 32 including a processor 80 having control logic 82 configured to implement the functions ascribed to the data management service 44 discussed herein in connection with FIGS. 1-4. The network element has a native or interfaced memory containing data and instructions to enable the processor to implement the functions ascribed to it herein. For example, the memory may contain software modules configured to perform the functions described above with respect to the scheduler/optimizer module 62, the policy module 64, the data source control module 66, the data target control module 68, the client notification module 70, and the security and AAA module 72. I/O ports 84 are also provided to enable the network element to receive requests, issue instructions regarding fulfilled requests, and otherwise communicate with other constructs in the network. Where special interface instructions are required to be supplied to the I/O ports or to the processor 80, modules containing these data and instructions may be included as well. In the illustrated embodiment, the network element 32 includes a data and client interfaces module 86 and a network resource manager interface module 88.

In the embodiment illustrated in FIG. 6, the network resources manager 46 is configured to be implemented on a network element 32 including a processor 90 having control logic 92 configured to implement the functions ascribed to the network resources manager discussed herein in connection with FIGS. 1-4. The network element, in this embodiment, has a native or interfaced memory containing data and instructions to enable the processor to implement the functions ascribed to it herein. For example, the memory may contain software modules configured to perform the functions described above with respect to the topology discovery module 50, the route creation module 52, the path allocation module 54, the scheduling and statistics module 56, the performance monitor 58, and the congestion resolution module 60. I/O ports 94 are also provided to enable the network element to receive requests, issue instructions regarding fulfilled requests, interface with network elements to fulfill requests, and otherwise communicate with other constructs in the network. A protocol stack 96 may be provided to enable the network resources manager to undertake protocol exchanges with other network elements on the network to enable it to perform network discovery and management, reserve resources on the network, and otherwise perform the functions ascribed to the network resource manager 46 on the network.

The control logic 82, 92, may be implemented as a set of program instructions that are stored in a computer readable memory within the network element and executed on a microprocessor, such as processor 80, 90. However, it will be apparent to a skilled artisan that all logic described herein can be embodied using discrete components, integrated circuitry such as an Application Specific Integrated Circuit (ASIC), programmable logic used in conjunction with a programmable logic device such as a Field Programmable Gate Array (FPGA) or microprocessor, or any other device including any combination thereof. Programmable logic can be fixed temporarily or permanently in a tangible medium such as a read-only memory chip, a computer memory, a disk, or other storage medium. Programmable logic can also be fixed in a computer data signal embodied in a carrier wave, allowing the programmable logic to be transmitted over an interface such as a computer bus or communication network. All such embodiments are intended to fall within the scope of the present invention.

It should be understood that various changes and modifications of the embodiments shown in the drawings and described herein may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A method of facilitating the transmission of medical images on a network, the method comprising the steps of:

receiving, from a client application, a transaction request relating to the delivery of at least one medical image from a data source to a data target on a network;

scheduling delivery of the medical image to occur at a scheduled point in the future, between the data source and the data target on the network, the step of scheduling comprising ascertaining a relative policy-based priority of the transaction request compared to other previously received transaction requests by determining, from the transaction request, an identity of an individual that issued the transaction request using the client application, where the individual was located when the transaction request was issued, and why the transaction request was issued, sorting all of the transaction requests that have been received and which have not yet started to be executed according to a policy-based priority, and allocating future timeslots to each transaction request to thereby enable the transaction requests to be scheduled over time for execution in the future according to their respective priorities;

reserving network resources on the network to enable the medical image to be delivered over the network from the data source to the data target at the scheduled time for execution;

interfacing the data source and data target to instruct the data source to transfer the data over the reserved network resources to the data target at the future scheduled time for the transaction request to thereby coordinate delivery of the medical image between the data source and data target;

monitoring the delivery of the medical image over the network; and adjusting the steps of scheduling and reserving, if necessary, to accommodate higher priority transaction requests that are subsequently received, the step of adjusting comprising determining which of the transaction requests that have been scheduled over time for execution in the future have a priority that is higher than the subsequently received transaction request (higher priority requests), determining which of the transaction requests that have been scheduled over time for execution in the future have a priority that is lower than the subsequently received transaction request (lower priority requests), and changing the scheduled time for execution of the lower priority transaction requests so that the subsequently received transaction request will be executed at a point in the future after the higher priority requests are executed and before the lower priority transaction requests are executed; and adjusting the steps of scheduling and reserving, if necessary to accommodate adverse network conditions, if the adverse network conditions delay execution of one or more transaction requests to prevent execution of the transaction requests from occurring as scheduled.

2. The method of claim 1, wherein the step of scheduling comprises understanding a work flow of transactions on the network.

3. The method of claim 2, wherein the step of understanding the work-flow comprises anticipating upcoming transaction requests from other transaction requests, statistics, or transaction patterns.

4. The method of claim 1, further comprising generating a histogram of traffic patterns on the network on at least one of a daily and weekly basis.

5. The method of claim 1, wherein the transaction request specifies a requested timing, and wherein the requested timing is under-constrained.

6. The method of claim 1, wherein the step of reserving network resources comprises setting a class of service for the transaction request.

7. The method of claim 1, wherein the step of reserving network resources comprises interfacing with network elements to allocate at least one of a route and a path through the network.

8. The method of claim 7, wherein the step of reserving network resources further comprises reserving bandwidth on the allocated route or path.

9. The method of claim 1, wherein the step of reserving network resources comprises rate-limiting medical image sourcing applications to prevent the medical image sourcing applications from transmitting medical images on the network.

* * * * *